US00PP23253P2

(12) United States Plant Patent
Danziger

(10) Patent No.: US PP23,253 P2
(45) Date of Patent: Dec. 11, 2012

(54) ***IMPATIENS* PLANT NAMED 'DANMU77'**

(50) Latin Name: *Impatiens walleriana*
Varietal Denomination: DANMU77

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/136,101

(22) Filed: Jul. 22, 2011

(51) Int. Cl.
*A01H 5/00* (2006.01)

(52) U.S. Cl. ..... Plt./317

(58) Field of Classification Search ..... Plt./317
See application file for complete search history.

*Primary Examiner* — Annette Para
(74) *Attorney, Agent, or Firm* — Cassandra Bright

(57) ABSTRACT

A new and distinct *Impatiens* cultivar named 'DANMU77' is disclosed, characterized by a compact, upright and mounding plant habit. Plants produce unique light pink, fully double flowers held just above the foliage. Plants flower and branch freely. The new variety is an *Impatiens*, normally produced as an outdoor garden or container plant.

2 Drawing Sheets

Figure 1:
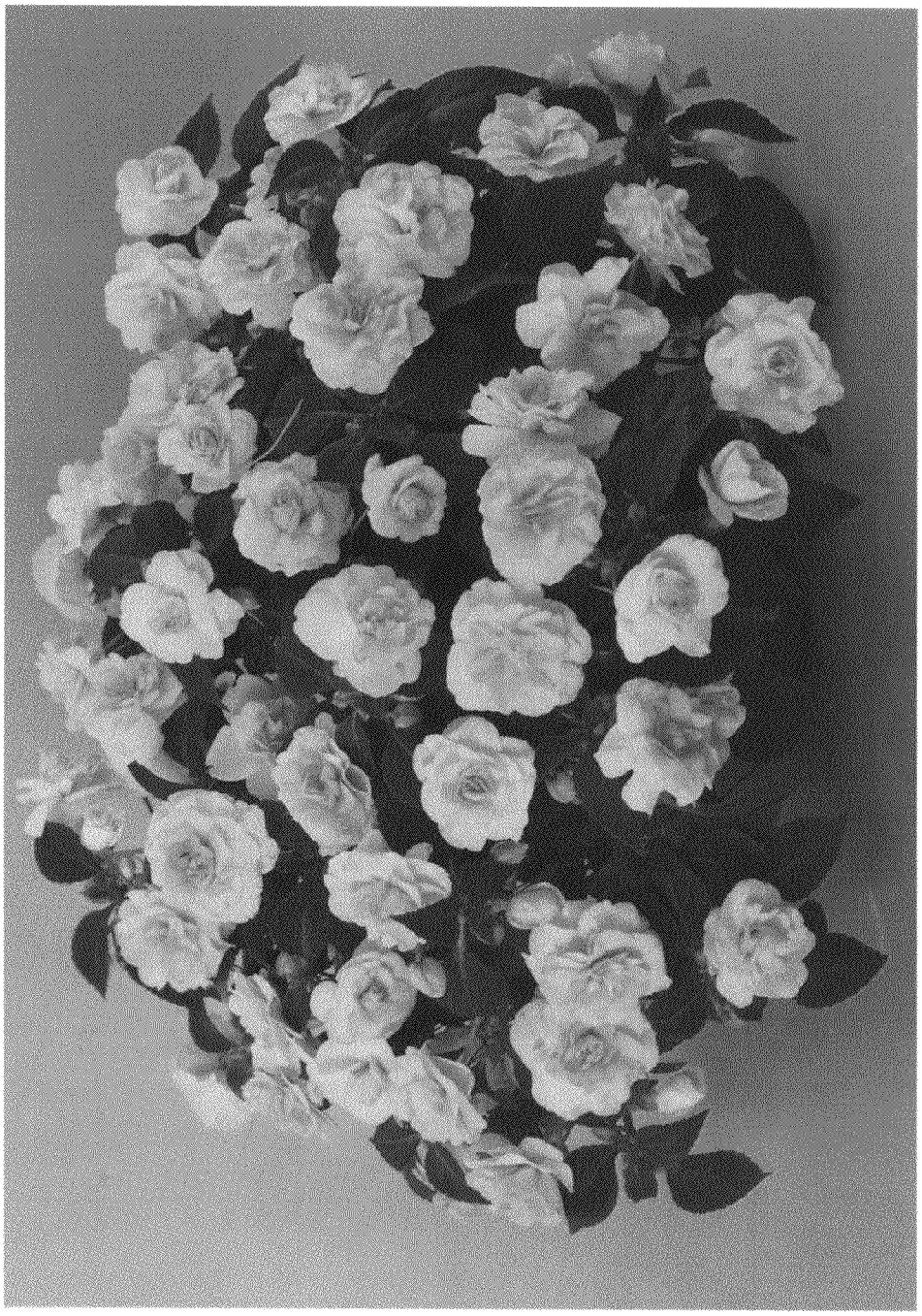

Latin name of the genus and species: *Impatiens walleriana.* Variety denomination: 'DANMU77'.

BACKGROUND OF THE INVENTION

The new *Impatiens* cultivar is a product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during November 2008.

The seed parent is the unpatented, proprietary seedling variety referred to as *Impatiens walleriana* '50V' The pollen parent is the unpatented proprietary seedling variety referred to as *Impatiens walleriana* '1293HF'. The new variety was discovered in April 2009 by the inventor in a group of seedlings resulting from the 2008 crossing, in a research greenhouse in Moshav Mishmar Hashiva, Israel.

Asexual reproduction of the new cultivar 'DANMU77' by vegetative cuttings was first performed at a research greenhouse in Moshav Mishmar Hashiva, Israel in April 2009 and has shown that the unique features of this cultivar are stable and reproduced true to type in successive generations.

SUMMARY OF THE INVENTION

The cultivar 'DANMU77' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANMU77' These characteristics in combination distinguish 'DANMU77' as a new and distinct *Impatiens* cultivar:

1. Compact, upright and mounding growth habit
2. Unique light pink, fully double flowers held just above foliage
3. Free branching
4. Free flowering
5. Bright green foliage Plants of the new cultivar 'DANMU77' are similar to plants of the seed parent, *Impatiens walleriana* '50V' in most horticultural characteristics, however, plants of the new cultivar 'DANMU77' produce flowers that are fully double, whereas the seed parent produces single, 5 petaled flowers. Additionally, the new variety has lighter colored flowers and foliage than the seed parent.

Plants of the new cultivar 'DANMU77' are similar to plants of the pollen parent, *Impatiens walleriana* 'CV444' in most horticultural characteristics, however, plants of the new cultivar 'DANMU77' produce flowers that are fully double, whereas the pollen parent produces single, 5 petaled flowers. Additionally, plants of the new variety are less vigorous than the pollen parent.

COMMERCIAL COMPARISON

Plants of the new cultivar 'DANMU77' are comparable to the variety *Impatiens* 'DANMU16', unpatented. The two *Impatiens* varieties are similar in most horticultural characteristics however, the new variety 'DANMU77' differs in having a lighter flower color, less vigorous growth habit, and different foliage coloring.

Plants of the new cultivar 'DANMU77' are comparable to the variety *Impatiens* 'DANMU12', unpatented. The two *Impatiens* varieties are similar in most horticultural characteristics however, the new variety 'DANMU77' differs in having a lighter flower color, smaller flower size, and different foliage coloring.

BRIEF DESCRIPTION OF THE PHOTOGRAPHS

The accompanying photograph in FIG. 1 illustrates in full color a typical plant of 'DANMU77' grown in a greenhouse, in a 12 cm pot. Age of the plant photographed is approximately 8 weeks from a rooted cutting.

Figure 2:
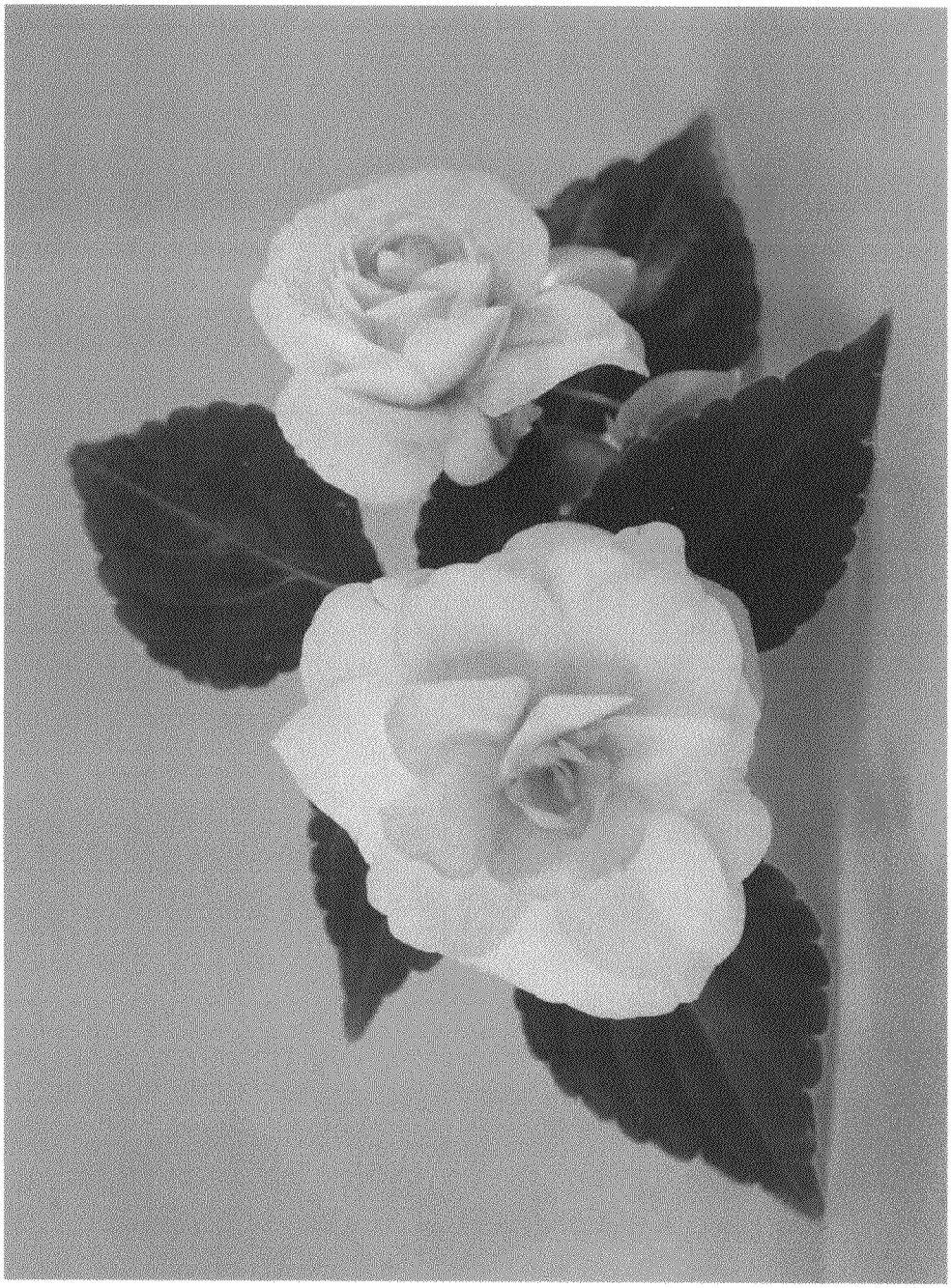

FIG. 2 illustrates in full color a close up of a typical bloom of 'DANMU77'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DANMU77' plants grown in a greenhouse during Winter in Moshav Mishmar Hashiva, Israel. The growing temperature ranged from 23° C. to 28° C. during the day and from 18° C. to 22° C. during the night. General light conditions are bright, normal sunlight. Measurements and numerical values represent averages of typical plant types.

Botanical classification: *Impatiens walleriana* 'DANMU77'.

PROPAGATION

Time to initiate roots:
- *Summer.*—7 to 10 days at approximately 25° C.
- *Winter.*—10 to 15 days at approximately 21° C.

Root description: Fibrous.

PLANT

Growth habit: Compact, upright and mounded.
Pot size of plant described: 12 cm.
Height: 15 cm.
Plant spread: 30 cm.
Growth rate: Rapid.
Branching characteristics: Basal-branching.
Length of primary lateral branches: 13 cm.
Quantity of primary lateral branches: 8 to 10.
Characteristics of primary lateral branches:
- *Form.*—Rounded.
- *Diameter.*—Approximately 0.7 cm.
- *Color.*—Near RHS Green 143C.
- *Texture.*—Smooth.
- *Strength.*—Strong, very stable.

Internode length: About 2.5 cm.

FOLIAGE

Leaf:
- *Arrangement.*—Alternate.
- *Quantity.*—Approximately 12 per branch.
- *Average length.*—4 cm.
- *Average width.*—2.5 cm.
- *Shape of blade.*—Ovate.
- *Apex.*—Acute.
- *Base.*—Acute.
- *Margin.*—Serrulate.
- *Texture of top surface.*—Smooth.
- *Pubescence.*—Absent.
- *Aspect.*—About 45°.
- *Color.*—Green. Young foliage upper side: RHS Green 137 A. Young foliage under side: RHS Green 138B. Mature foliage upper side: RHS Green 137A. Mature foliage under side: RHS Green 138 B.
- *Venation.*—Midrib with secondary veins on the lower surface with no prominent veins on the upper surface. Type: Pinnate. Venation color upper side: RHS Green 138A. Venation color under side: RHS Green 138B.
- *Petiole.*—Length: About 1.0 to 1.5 cm. Diameter: About 1 mm. Color: Near RHS Green 138B. Texture: Smooth.

FLOWER

Natural flowering season: Spring until fall in outdoor conditions.
Days to flowering from rooted cutting: 6 weeks.
Inflorescence and flower type and habit: Fully double flowers.
Rate of flower opening: 6 to 8 days from bud to fully opened flower.
Flower longevity on plant: 8 days.
Persistent or self-cleaning: Not persistent.
Bud:
- *Shape.*—Rounded.
- *Length.*—About 1 cm.
- *Diameter.*—About 0.5 cm.
- *Color.*—Near RHS Yellow-Green 145C.

Flower size:
- *Diameter.*—About 4.5 cm.
- *Depth.*—About 2 cm.

Petals:
- *Quantity.*—About 30 to 35 Petals.
- *Arrangement.*—Imbricate.
- *Length.*—About 2 cm.
- *Width.*—About 1.5 cm.
- *Shape.*—Obcordate.
- *Apex.*—Retuse.
- *Base.*—Acute.
- *Margin.*—Entire.
- *Texture, upper and lower surfaces.*—Smooth.
- *Color.*—When opening upper surface: Near RHS Red-Purple 62C. When opening, lower surface: Near RHS Red 56C. Fully opened, upper surface: Near RHS Red-Purple 65D. Fully opened, lower surface: Near RHS White N 155B.

Spurs:
- *Quantity per flower.*—1.
- *Length.*—3 cm.
- *Diameter.*—0.1 cm.
- *Aspect.*—Spur curvature 40° to 45° from peduncle.
- *Color.*—Towards base: Near RHS Yellow-Green 152 D. Apex: Near RHS Yellow-Green 152 B.

Sepals:
- *Quantity.*—4.
- *Length.*—Two large sepals, length about 1 cm. Two small sepals, length 0.3 cm.
- *Width.*—Large sepals: About 0.5 cm. Small sepals: about 0.2 cm.
- *Shape.*—Large sepals: Oblong. Small sepals: acicular Apex: Acute. Base: large sepals: rounded. Small sepals: acuminate.
- *Margin.*—Entire.
- *Color.*—Small sepals near RHS Yellow-Green 147 C. Large sepals near RHS Yellow-Green 145 B.

Peduncles:
- *Length.*—About 2 cm.
- *Diameter.*—0.1 cm.
- *Angle.*—About 45° to the lateral branch.
- *Strength.*—Stable, flexible.
- *Texture.*—Smooth.
- *Color.*—Near RHS Yellow-Green 145A.

Fragrance: None.

REPRODUCTIVE ORGANS

Sterile, no reproductive organs.

OTHER CHARACTERISTICS

Seeds and fruits: Not observed, sterile flowers.
Disease/pest resistance: Neither resistance nor susceptibility to pathogens and pests common to *Impatiens* have been observed.
Temperature tolerance: The new variety tolerates low temperatures to 10° C., maximum temperature tolerance unknown.

What is claimed is:

1. A new and distinct cultivar of *Impatiens* plant named 'DANMU77' as herein illustrated and described.

* * * * *